United States Patent
Sanganbhatla et al.

(10) Patent No.: US 7,777,053 B2
(45) Date of Patent: Aug. 17, 2010

(54) EFFICIENT PROCESS FOR PRODUCTION OF CARVEDILOL PHOSPHATE

(75) Inventors: Shankar Sanganbhatla, Navi Mumbai (IN); Jitendra Pandurang Suryavanshi, Mumbai (IN); Alam Sayyed Zahid, Pune (IN)

(73) Assignee: Wanbury Limited, Navi-Mumbai (IN)

( * ) Notice: Subject to any disclaimer, the term of this patent is extended or adjusted under 35 U.S.C. 154(b) by 119 days.

(21) Appl. No.: 11/936,634

(22) Filed: Nov. 7, 2007

(65) Prior Publication Data
US 2008/0287688 A1 Nov. 20, 2008

(30) Foreign Application Priority Data
May 17, 2007 (IN) .................. 929/MUM/2007

(51) Int. Cl.
*C07D 209/82* (2006.01)
(52) U.S. Cl. ...................................... 548/444
(58) Field of Classification Search .................. 548/444
See application file for complete search history.

(56) References Cited

U.S. PATENT DOCUMENTS
4,503,067 A 3/1985 Wiedemann et al.
2005/0277689 A1* 12/2005 Brook et al. ................ 514/411

* cited by examiner

*Primary Examiner*—Rei-tsang Shiao
(74) *Attorney, Agent, or Firm*—Proteus Patent Practice LLC; Henry E. Auer

(57) ABSTRACT

A novel cost effective process for the synthesis of phosphate salts of 1-(9H-carbazol-4yloxy)-3-[[2-(2-methoxyphenoxy) ethyl]amino]-propan-2-ol, (carvedilol phosphate) of formula (II) with high yields and purity is disclosed. More particularly, the invention discloses a process for preparation of crystalline phosphate salts of carvedilol using various phosphate forming reagents such as phosphorous pentoxide, polyphosphoric acid, dipotassium hydrogen phosphate, ammonium dihydrogen ortho phosphate, and sodium dihydrogen ortho phosphate in solvents selected from Acetonitrile, acetone and tetrahydrofuran. The solvents used to prepare solvates of carvedilol dihydrogen phosphate are methanol, ethanol and isopropyl alcohol.

11 Claims, No Drawings

EFFICIENT PROCESS FOR PRODUCTION OF CARVEDILOL PHOSPHATE

TECHNICAL FIELD

The present invention relates to a novel cost effective process for the synthesis of phosphate salts of 1-(9H-carbazol-4yloxy)-3-[[2-(2-methoxyphenoxy)ethyl]amino]-propan-2-ol, (carvedilol phosphate) of formula (II) with high yields and purity. More particularly, the invention relates to a process for preparation of crystalline phosphate salts of carvedilol using various phosphate forming reagents such as phosphorous pentoxide (also termed phosphorus pentoxide), polyphosphoric acid, dipotassium hydrogen phosphate, ammonium dihydrogen ortho phosphate (also termed orthophosphate or phosphate), and sodium dihydrogen ortho phosphate in solvents selected from acetonitrile, acetone and tetrahydrofuran. The solvents used to prepare solvates of carvedilol dihydrogen phosphate are methanol, ethanol and isopropyl alcohol.

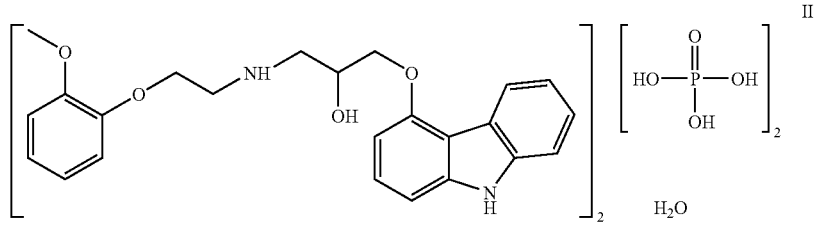

II

BACKGROUND OF INVENTION

Carvedilol, the first beta blocker labeled in the United States for the treatment of heart failure, has been shown to improve left ventricular ejection fraction and may reduce mortality. Carvedilol is chemically known as 1-(9H-carbazol-4yloxy)-3-[[2-(2-methoxyphenoxy)-ethyl]amino]-propan-2-ol, which has the following structure (I).

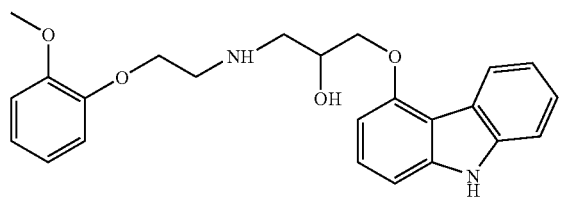

I

Carvedilol is disclosed in U.S. Pat. No. 4,503,067 to Wiedemann et al. Carvedilol is indicated in the management of congestive heart failure (CHF), as an adjunct to conventional treatments (ACE inhibitors and diuretics). Currently, carvedilol is used for treating patients suffering with hypertension, congestive heart failure and angina. The use of carvedilol has been shown to provide additional morbidity and mortality benefits in CHF (Packer et al., 2002).

Carvedilol is synthesized as a racemic mixture of R (+) and S (−) enantiomers for incorporation in medication that is available commercially as a free base. The free base exhibits nonselective beta.-adrenoreceptor blocking activity by virtue of the S (−) enantiomer and also exhibits alpha.-adrenergic blocking activity by virtue of both R (+) and S(−) enantiomers.

Carvedilol contains an α-hydroxyl secondary amine functional group, which has a pKa of 7.8. Carvedilol exhibits predictable solubility behavior in neutral or alkaline media, i.e. above pH of 9.0, the solubility of carvedilol is relatively low (<1 μg/ml). The solubility of carvedilol increases with decreasing pH and reaches a plateau near pH=5, i.e. where saturation solubility is about 23 μg/ml. at pH=7 and about 100 μg/ml at pH=5 at room temperature. At lower pH values (i.e. at a pH of 1 to 4 in various buffer systems), solubility of carvedilol is limited by the solubility of its protonated salts.

The presence of the α-hydroxyl secondary amine group in the carvedilol chemical structure confers a propensity upon the compound to chemically react with excipients normally included in a dosage form to aid manufacture, maintain quality, or enhances dissolution rate. For example, the α-hydroxyl secondary amine group of carvedilol can react with aldehydes or ester functional groups associated with conventionally used excipients, which may include esters, aldehydes and/or other chemical residue functional groups. This often results in marginal or unacceptable chemical stability upon storage.

US patent 2005/0277689 A1 describes the synthesis of carvedilol phosphate (II) carried out by treating carvedilol with o-phosphoric acid in acetone, acetone-water mixture to prepare the crystalline salt, and with methanol, isopropyl alcohol to prepare a solvate of carvedilol phosphate.

U.S. Patent Application 2005/0277689 A1 describes that carvedilol phosphate exhibits much higher aqueous solubility. A novel crystalline form is also disclosed having potential to improve the stability of carvedilol in formulations due to the fact that the secondary amine functional group attached to the carvedilol core structure, a moiety pivotal to degradation processes, is protonated as a salt.

In light of the foregoing, a salt, of carvedilol with greater aqueous solubility, chemical stability, etc. would offer many potential benefits for provision of medicinal products containing the drug carvedilol. Such benefits would include products with the ability to achieve desired or prolonged drug levels in a systemic system by sustaining absorption along the gastro-intestinal tract of mammals (i.e., such as humans), particularly in regions of neutral pH, where a drug, such as carvedilol, has minimal solubility.

The present invention is directed to providing another convenient and robust, rugged process for the preparation of carvedilol phosphate.

SUMMARY OF THE INVENTION

Accordingly, the present invention discloses a novel process for production of carvedilol phosphate salts with high yields and purity. The phosphate salts of carvedilol which includes carvedilol dihydrogen phosphate and solvates of the dihydrogen phosphate salt of carvedilol. The process of the present invention involves the reaction of carvedilol with various phosphate forming reagents such as phosphorous pentoxide, polyphosphoric acid, dipotassium hydrogen phosphate, ammonium dihydrogen ortho phosphate, sodium dihydrogen ortho phosphate to prepare carvedilol phosphate.

This phosphate salt forming reaction is carried out using solvents such as acetone, acetonitrile, tetrahydrofuran for the preparation of crystalline carvedilol dihydrogen phosphate salt, and alcohols such as methanol, ethanol, isopropyl alcohol for the preparation of solvates of carvedilol dihydrogen phosphate. The process of the present invention is simple to operate, high yielding and is easily scalable to industrial production.

DETAILED DESCRIPTION OF THE INVENTION

The invention will now be described in detail in connection with certain preferred and optional embodiments, so that various aspects thereof may be more fully understood and appreciated. Equivalents that provide the present invention are also contemplated herein.

This invention provides a novel cost effective preparation of phosphate salts of carvedilol with high yields and purity. The process of the present invention is simple to operate, high yielding and easily scalable to industrial production.

Accordingly, an embodiment of a process for preparation of carvedilol dihydrogen phosphate hemihydrate comprises the steps of:
a) dissolving carvedilol free base in suitable solvent and water mixture;
b) generating a phosphate salt of the carvedilol using a suitable phosphate forming agent selected from the group consisting of phosphorous pentoxide, polyphosphoric acid, dipotassium hydrogen phosphate, ammonium dihydrogen ortho phosphate or sodium dihydrogen ortho phosphate at a temperature range of 35 to 50° C. for a period of 30 mins to 2 hrs; and
c) isolating the carvedilol dihydrogen phosphate hemihydrate salt from the reaction mass.

The phosphate forming agent is selected from the group consisting of phosphorous pentoxide (also termed phosphorus pentoxide), polyphosphoric acid, dipotassium hydrogen phosphate, ammonium dihydrogen ortho phosphate (also termed orthophosphate or phosphate) or sodium dihydrogen ortho phosphate. The phosphate forming reaction is carried out at a temperature range of 35 to 50° C. for a period of 30 mins to 2 hrs.

The solvent suitable for preparation of carvedilol dihydrogen phosphate is a solvent in which carvedilol is soluble. The solvents suitable to prepare crystalline carvedilol dihydrogen phosphate are selected from acetone, tetrahydrofuran or acetonitrile, and to prepare solvates of carvedilol phosphates are selected from methanol, ethanol or isopropanol.

Thus, the phosphate salts of carvedilol include carvedilol dihydrogen phosphate and solvates of the dihydrogen phosphate salt of carvedilol.

The phosphate forming reagent is used in about a 1:1 molar ratio with reference to the substrate, carvedilol. The phosphate forming reaction is carried out preferably at a temperature of 45 to 50° C. for 30 mins to 2 hrs to yield carvedilol dihydrogen phosphate salt.

The preferred embodiment of the present invention comprises preparation of phosphate salts of carvedilol which include all the above mentioned phosphate forming reagents and solvents in which carvedilol is soluble but not intended to limit, in any way, the scope of the present invention.

In one embodiment, the invention provides a process for preparation of carvedilol dihydrogen phosphate dehydrate using phosphorous pentoxide in a reaction medium of acetone and water. The reaction is carried out at 35 to 50° C. for a period of 30 mins to 2 hrs. The solid precipitated is stirred at 0-5° C. and then filtered. The collected solid is washed with aq. acetone and dried under vacuum to obtain a constant weight.

In another embodiment, the invention provides a process for preparation of methanol solvate of carvedilol dihydrogen phosphate using phosphorous pentoxide in a reaction medium of methanol and water. The reaction is carried out at 35 to 50° C. for a period of 30 mins to 2 hrs. The solid product precipitated is stirred at 0-5° C. and then filtered. The collected solid is washed with aqueous acetone and dried under vacuum to obtain a constant weight.

In a similar manner, carvedilol dihydrogen phosphate hemihydrate and solvates of phosphate salts are prepared using different phosphate forming reagents and various suitable organic solvents as described above. The Examples set forth below, while illustrative of the present invention, are not intended to limit, in any way, the scope of the present invention.

EXAMPLES

Example 1

Preparation

Carvedilol Dihydrogen Phosphate Hemihydrate

A reactor was charged with 2520 ml acetone, 280 g carvedilol and 300 ml water. The contents of the reaction mass were cooled to 0-5° C. Phosphorous pentaoxide (50 g) was charged at 0-5° C. The temperature of the reaction mass was raised up to 40-45° C. and maintained for 60 mins. The contents were cooled to 0-5° C. The solid precipitate formed was stirred at 0-5° C., then filtered to collect cake. The cake was washed with aqueous acetone and dried under vacuum to a constant weight to obtain the crystalline salt of carvedilol dihydrogen phosphate salt. Yield: 336 g. (percentage yield is 95% on theoretical yield) Purity-99.7%.

Example 2

Example 1 was reproduced by replacing acetone with acetonitrile to obtain crystalline salt of carvedilol dihydrogen phosphate.

Example 3

Example 1 was reproduced by replacing acetone with tetrahydrofuran to obtain crystalline salt of carvedilol dihydrogen phosphate.

Example 4

Example 1 was reproduced by replacing acetone with Isopropyl alcohol to obtain isopropanol solvate of the carvedilol dihydrogen phosphate.

Example 5

Example 1 was reproduced by replacing acetone with methanol to obtain the methanol solvate of the carvedilol dihydrogen phosphate.

Example 6

A reactor was charged 2520 ml. acetone, 280 g. carvedilol and 300 ml water. The contents of reaction mixture were cooled to 0-5° C. Polyphosphoric acid (50 g). was charged at 0-5° C. The temperature of the reaction mass was raised up to 40-45° C. and maintained for 60 mins. The contents of the reaction mass were cooled to 0-5° C. The solid precipitate formed was stirred at 0-5° C., then filtered to collect the cake and washed with aqueous acetone to obtain the crystalline salt of carvedilol dihydrogen phosphate salt. The cake was dried under vacuum to a constant weight. Yield: 330 g. (percentage yield is 93.3% on theoretical yield) purity 99.7%

Example 7

Example 6 was reproduced by replacing acetone with acetonitrile to obtain crystalline salt of carvedilol dihydrogen phosphate.

Example 8

Example 6 was reproduced by replacing acetone with tetrahydrofuran to obtain crystalline salt of carvedilol dihydrogen phosphate.

Example 9

Example 6 was reproduced by replacing acetone with isopropyl alcohol to obtain isopropanol solvate of the carvedilol dihydrogen phosphate.

Example 10

Example 6 was reproduced by replacing acetone with methanol to obtain methanol solvate of carvedilol dihydrogen phosphate

Example 11

A reactor was charged with 2520 ml acetone, 280 g. carvedilol, 300 ml. water and 50 g dipotassium dihydrogen phosphate. The contents were cooled to 0-5° C. The pH of the reaction mass was adjusted to 4.5-5 with HCl. The reaction temperature was raised up to 40-45° C. and maintained for 60 mins. The contents of the reaction mass were cooled to 0-5° C. The solid precipitate formed was stirred at 0-5° C., then filtered to collect the cake and washed with aqueous acetone to obtain the crystalline salt of carvedilol dihydrogen phosphate salt. The cake was dried under vacuum to a constant weight. Yield: 334 g. (percentage yield is 94.49% on theoretical yield) Purity: 99.7%.

Example 12

Example 11 was reproduced by replacing acetone with acetonitrile to obtain crystalline salt of carvedilol dihydrogen phosphate.

Example 13

Example 11 was reproduced by replacing acetone with tetrahydrofuran to obtain crystalline salt of carvedilol dihydrogen phosphate.

Example 14

Example 11 was reproduced by replacing acetone with Isopropyl alcohol to obtain isopropanol solvate of the carvedilol dihydrogen phosphate.

Example 15

Example 11 was reproduced by replacing acetone with methanol to obtain methanol solvate of carvedilol dihydrogen phosphate.

Example 16

Example 11 was reproduced by replacing dipotassium dihydrogen phosphate with ammonium dihydrogen ortho phosphate in acetone to obtain crystalline salt of carvedilol dihydrogen phosphate.

Example 17

Example 16 was reproduced by replacing acetone with acetonitrile to obtain crystalline salt of carvedilol dihydrogen phosphate.

Example 18

Example 16 was reproduced by replacing acetone with tetrahydrofuran to obtain crystalline salt of carvedilol dihydrogen phosphate.

Example 19

Example 16 was reproduced by replacing acetone with isopropyl alcohol to obtain isopropanol solvate of carvedilol dihydrogen phosphate.

Example 20

Example 16 was reproduced by replacing acetone with methanol to obtain methanol solvate of carvedilol dihydrogen phosphate.

Example 21

Example 11 was reproduced by replacing dipotassium dihydrogen phosphate with sodium dihydrogen ortho phosphate to obtain crystalline salt of carvedilol dihydrogen phosphate.

Example 22

Example 21 was reproduced by replacing acetone with acetonitrile to obtain crystalline salt of carvedilol dihydrogen phosphate.

Example 23

Example 21 was reproduced by replacing acetone with tetrahydrofuran to obtain crystalline salt of carvedilol dihydrogen phosphate.

Example 24

Example 21 was reproduced by replacing acetone with Isopropyl alcohol to obtain isopropanol solvate of carvedilol dihydrogen phosphate.

Example 25

Example 21 was reproduced by replacing acetone with methanol to obtain methanol solvate of carvedilol dihydrogen phosphate.

It is to be understood that the invention is not limited to the embodiments illustrated here in above and the right is reserved to the illustrated embodiments and all modifications coming within the scope of the following claims.

We claim:

1. An efficient process for preparation of carvedilol dihydrogen phosphate hemihydrate salt in high yield comprising the steps of:
   a) dissolving carvedilol free base in a suitable solvent and water mixture;
   b) generating a phosphate salt of the carvedilol using a suitable phosphate forming agent selected from the group consisting of phosphorous pentoxide (phosphorus pentoxide), polyphosphoric acid, dipotassium hydrogen phosphate, ammonium dihydrogen ortho phosphate and sodium dihydrogen ortho phosphate to obtain carvedilol dihydrogen phosphate salt; and
   c) isolating the carvedilol dihydrogen phosphate hemihydrate salt from the reaction mass.

2. The process as claimed in claim 1, wherein the phosphate forming agent used in the preparation of the salt comprises phosphorous pentoxide.

3. The process as claimed in claim 1, wherein the phosphate forming agent used in the preparation of the salt comprises polyphosphoric acid.

4. The process as claimed in claim 1, wherein the phosphate forming agent used in the preparation of the salt comprises dipotassium hydrogen phosphate.

5. The process as claimed in claim 1, wherein the phosphate forming agent used in the preparation of the salt comprises ammonium dihydrogen ortho phosphate.

6. The process as claimed in claim 1, wherein the phosphate forming agent used in the preparation of the salt comprises sodium dihydrogen ortho phosphate.

7. The process as claimed in claim 1, wherein said solvent used in the salt preparation is acetonitrile.

8. The process as claimed in claim 1, wherein said solvent used in the salt preparation is tetrahydrofuran.

9. The process as claimed in claim 1, wherein said solvent used in the salt preparation is acetone.

10. The process as claimed in claim 1, wherein carvedilol phosphate is isolated with a yield of at least about 93%.

11. The process as claimed in claim 1 wherein the generating is carried out at a temperature in the range from 35 to 50° C. for a time period of 30 mins to 2 hrs.

\* \* \* \* \*